US006197946B1

(12) United States Patent
Cottingham et al.

(10) Patent No.: US 6,197,946 B1
(45) Date of Patent: *Mar. 6, 2001

(54) PEPTIDE PRODUCTION AS FUSION PROTEIN IN TRANSGENIC MAMMAL MILK

(75) Inventors: Ian Robert Cottingham; Ian Garner, both of Edinburgh (GB)

(73) Assignee: PPL Therapeutics (Scotland) Limited, Edinburgh (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/938,595

(22) Filed: Sep. 25, 1997

Related U.S. Application Data

(62) Division of application No. 08/727,153, filed on Oct. 8, 1996, which is a continuation of application No. 08/718,523, filed as application No. PCT/GB95/00769 on Apr. 5, 1995, now abandoned.

(30) Foreign Application Priority Data

Apr. 8, 1994 (GB) .................................................. 9406974

(51) Int. Cl.$^7$ ........................... C07H 21/04; C12P 21/02; C12N 15/62; C12N 15/85
(52) U.S. Cl. ....................... 536/23.4; 536/23.1; 536/23.5; 800/4; 800/7; 435/455
(58) Field of Search .................................. 536/23.5, 23.1, 536/23.4; 435/69.1, 172.3, 320.1, 455; 935/11, 33, 34, 47; 530/300, 301, 302, 306–316; 800/4, 7

(56) References Cited

U.S. PATENT DOCUMENTS

| | | | | |
|---|---|---|---|---|
| 4,457,864 | * | 7/1984 | Hruby | 260/112.5 R |
| 5,366,894 | * | 11/1994 | Clark et al. | 435/320.1 |
| 5,607,676 | * | 3/1997 | Gevas | 424/197.11 |
| 5,620,923 | | 4/1997 | Rechsteiner et al. | 435/69.7 |
| 5,827,690 | | 10/1998 | Meade et al. | 435/69.6 |
| 6,010,883 | * | 1/2000 | Nagai et al. | 435/69.7 |

FOREIGN PATENT DOCUMENTS

| | | |
|---|---|---|
| 0 590 530 A2 | 4/1994 | (EP) . |
| 0 771 874 A2 | 5/1997 | (EP) . |
| WO 88/00239 | 1/1988 | (WO) . |
| WO 90/05188 | 5/1990 | (WO) . |
| WO 92/11358 | 7/1992 | (WO) . |
| WO 92/22644 | 12/1992 | (WO) . |
| WO 94/04672 | 3/1994 | (WO) . |

OTHER PUBLICATIONS

Van Heeke, Protein Expression and Purification 4:265–274, 1993.*
Clark. A. J., et al., "Rescuing Transgene Expression by Co–integration," Bio/Technol. 10:1450–1454 (1992).
Eipper, B. A., et al., "The Biosynthesis of Neuropeptides: Peptide α–amidation," Annu. Rev. Neurosci. 15:57–85 (1992).
Eipper, B. A., et al., "Peptidylglycine α–amidating monooxygenase: A multifunctional protein with catalytic, processing, and routing domains," Protein Sci. 2:489–497 (Apr. 1993).
Han, K.–K., et al., "Current Developments in Chemical Cleavage of Proteins," Int. J. Biochem. 15(7):875–884 (1983).
Houdebine, L.–M., "Production of pharmaceutical proteins from transgenic animals," J. Biotechnol. 34 (3):269–287 (May 31, 1994).
Lindahl, L., and Vogel, H. J., "Metal–Ion–Dependent Hydrophobic–Interaction Chromatography of a α–Lactalbumins," Anal. Biochem. 140:394–402 (1984).
Paleyanda, R.K. et al., "Transgenic pigs produce functional human factor VIII in milk," Nature Biotechnology 15 (10):971–975 (Oct. 1997).
Pursel, V.G., et al., "Genetic Engineering of Livestock,," Science 244:1281–1288 (1989).
Pursel, V. G., and Rexroad, C. E., Jr., "Status of Research with Transgenic Farm Animals," J. Anim. Sci. 71(Suppl. 3):10–19 (Mar. 1993).
Ray, M. V., et al., "Production of Racombinant Salmon Calcitionin by In Vitro Amidation of an Escherichia coli Produced Precursor Peptide," Bio/Technol. 11:64–70 (Jan. 1993).
Wold, F., "In Vivo Chemical Modification of Proteins (Post-–Translation Modification)," Ann. Rev. Biochem. 50:783–814 (1981).
Wright, G., et al., "High Level Expression of Active Human Alpha–1–Antitrypsin in the Milk of Transgenic Sheep," Bio/Technol. 9:830–834 (1991).
English language abstract of EP 0 590 530 A1 Apr. 6, 1994.
Clark, A.J., "Transgenic animals and the manipulation of milk composition," Animal Genetics 20:327–328 (1989).
Clark, A.J., et al., "Expression of Human Anti–hemophilic Factor IX in the Milk of Transgenic Sheep," Bio/Technology 7:487–492 (may 1989).

(List continued on next page.)

Primary Examiner—Deborah J.R. Clark
(74) Attorney, Agent, or Firm—Sterne, Kessler, Goldstein & Fox P.L.L.C.

(57) ABSTRACT

Peptides can be produced in and purified from the milk of transgenic animals. The peptides are made as fusion proteins with a suitable fusion partner such as α-lactalbumin, which is a natural milk protein. The fusion partner protein acts to promote secretion of the peptides and, at least in the case of α-lactalbumin, allows a single-step purification based on specific affinity. The peptide is released from the purified fusion protein by a simple cleavage step and purified away from the now liberated α-lactalbumin by repeating the same affinity purification method. A particular advantage of producing peptides via this route, in addition to the obvious advantages of high yield and biocompatibility, is that specific post-translational modifications, such as carboxy terminal amidation, can be performed in the mammary gland.

12 Claims, No Drawings

OTHER PUBLICATIONS

Ibrahimi, I.M., et al., "Determinants for protein translocation across mammalian endoplasmic reticulum. Membrane insertion of truncated and full –length prelysozyme molecules," *Eur. J. Biochem.* 155:571–576 (1986).

Okun. M.M., et al., "Truncation of a Secretory Protein Define Minimum Lengths Required for Binding to Signal Recognition Particle and Translocation across the Endoplasmic Reticulum Membrane," *J. Bio. Chem.* 265:7478–7484 (may 1990).

Prasad, R.V., et al., "Amino Acid Sequence of Rat α–Lactalbumin: A Unique α–Lactalbumin," *Biochemistry* 21:1479–1482 (1982).

* cited by examiner

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 4 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:1:

Gly Ala Pro Ala
1

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:2:

Ile Glu Gly Arg
1

```
(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:3:

Asp Asp Asp Asp Lys
1               5

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:4:

Phe Pro Thr Asp Asp Asp Asp Lys
1               5

(2) INFORMATION FOR SEQ ID NO:5:

(i) SEQUENCE CHARACTERISTICS:
        (A) LENGTH: 12 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:5:

Gly Ala Pro Ala Phe Pro Thr Asp Asp Asp Asp Lys
1               5                   10
```

PEPTIDE PRODUCTION AS FUSION PROTEIN IN TRANSGENIC MAMMAL MILK

CROSS REFERENCE TO RELATED APPLICATIONS

This application is a divisional of U.S. application Ser. No.08/727,153, filed Oct. 8, 1996 (pending), which is a continuation of U.S. application Ser. No. 08/718,523, filed Oct. 8, 1996 (now abandoned), which corresponds to International Application No. PCT/GB95/00769, filed Apr. 5, 1995.

BACKGROUND OF THE INVENTION

1. Field of the Invention

This invention relates to the production of peptides in the milk of transgenic mammals, particularly non-human placental mammals.

2. Related Art

Polymers of naturally occurring amino acids concatenated via their amino and carboxyl groups form the basis of many different biologically important compounds. Polymers of 3 to 100 amino acids are generally called peptides whilst larger concatamers are termed proteins. This is a purely arbitrary distinction, and the term "peptide" will be generally used throughout this specification even though the definition of peptides is not restricted to polymers of any particular size. Peptides can be biologically active without further modification or they can form the building blocks for more complex molecules by chemical incorporation into larger structures or by modification such as glycosylation. The term "peptide" is used herein to include biologically active or inactive molecules which may or may not be further modified by either chemical methods or in biological systems.

The direct chemical synthesis of peptides is expensive due to the cost of reagents and the high degree of purification needed to remove failed sequences. Microbial synthesis by recombinant DNA technology is not always appropriate for peptides, because of difficulties in their extraction and purification and the absence in the microbial host of enzymes for performing appropriate and correct post-translational modification. Heterologous proteins can be produced in stably transfected mammalian cell lines. Many such cell lines are available today and are used commercially, but concern remains that the cell lines were in general established from tumours of various types. More recently, the production of proteins in the milk of transgenic mammals such as sheep has become a reality, as illustrated in WO-A-8800239 and WO-A-9005188.

This invention relates to an economical process for the bulk production of peptides in the milk of transgenic animals. The production of peptides in milk is ideal as a bulk process because very large volumes of milk can be harvested using simple and environmentally safe technology. A second advantage of using transgenic technology is that only biologically safe materials are produced. This is in contrast to chemical methods where side reactions may produce toxic materials which can only be removed at additional cost.

Another advantage of using a biological process is that some reactions which can be essential for biological activity, for example carboxy-terminal amidation, are difficult to perform in good yield by chemical means. Carboxy-terminal amidation is catalysed by a specific enzyme which recognises and modifies peptides or proteins with a glycine residue at the carboxy terminus ("Peptidylglycine α-Amidating Monooxygenase: A Multifunctional Protein with Catalytic, Processing and Routing Domains" Eipper, B. A et al. (1993) Protein Science 2, 489–497). Therefore, suitably designed proteins will be specifically amidated before secretion into the milk of producer animals. This is only one example of a range of post-translational modifications which can be carried out by the biosynthetic pathways in the mammary gland and which can potentially be harnessed for the synthesis of particular peptide entities. Other examples of desirable post-translational modifications include disulphide bridge formation, γ-carboxylation of glutamic acid residues and the addition of O- and N-linked glycosylation ("In Vivo Chemical Modification of Proteins", Wold, F., *Ann. Rev. Biochem.* 50 783–814 (1981)).

The technology for producing large quantities of recombinant proteins, as opposed to shorter peptides, in milk is well established. The human protease inhibitor $\alpha_1$-antitrypsin, for example, has been produced in the milk of transgenic sheep at levels in excess of thirty grams of protein per liter ("High Level Expression of Active Human $\alpha_1$-Antitrypsin in the Milk of Transgenic Sheep" Wright, G. et al. (1991) *Bio/Technology*, 9 77–84). It is expected that the same technology can be applied to the production of proteins in cattle which can routinely produce up to 10,000 liters of milk per lactation.

BRIEF SUMMARY OF THE INVENTION

Production of proteins in the milk of transgenic producer animals is extremely advantageous in that, providing the protein is actually secreted by the mammary gland into the milk, no cellular extraction step is necessary. Nonetheless, the protein in question does, in many applications of the technology, have to be extracted from the milk produced, and it is to this problem that the present invention is particularly addressed. The invention also addresses the problem of the production of peptides, particularly relatively short peptides, whose properties may be such that they would normally interfere with their production.

DETAILED DESCRIPTION OF THE INVENTION

According to a first aspect of the invention, there is provided a process for the production of a peptide, the process comprising expressing in the milk of a transgenic non-human placental mammal a fusion protein comprising the peptide linked to a fusion partner protein, separating the fusion protein from the milk and cleaving the fusion protein to yield the peptide.

The reasons for producing the desired peptide as a fusion protein are essentially three-fold. First, it is expected that the established technology for producing relatively large proteins in milk will be applicable to the production of corresponding fusion proteins in which a peptide has been fused to the original protein. A second function of the fusion partner is to disguise properties of the peptide which might otherwise interfere with its production. Thirdly, the fusion partner may facilitate purification from milk by providing the peptide as part of a larger molecule. Milk is a complex biological fluid which contains fats, sugars, proteins and also peptides and proteolytic fragments, so the purification of synthetic peptides from such a mixture would be complex and expensive.

The use of living organisms as the production process means that all of the material produced will be chemically identical to the natural product. In terms of basic amino acid structures this means that only L-optical isomers, having the natural configuration, will be present in the product. Also the number of wrong sequences will be negligible because of the high fidelity of biological synthesis compared to chemical routes, in which the relative inefficiency of coupling reactions will always produce failed sequences. The absence of side reactions is also an important consideration with further modification reactions such as carboxy-terminal amidation. Again, the enzymes operating in vivo give a high degree of fidelity and stereospecificity which cannot be matched by chemical methods. Finally the production of peptides in a biological fluid means that low-level contaminants remaining in the final product are likely to be far less toxic than those originating from a chemical reactor.

Peptides producible by the invention are preferably from 3 to 100 amino acid residues in length, but the invention is not limited to the production of peptides of the preferred size range. The invention is particularly appropriate for producing α-amidated or other post-translationally modified peptides. Many peptides found in the nervous and endocrine systems of animals and bioactive peptides from other sources which have actions on the nervous system are α-amidated. Examples include the following, which are:

| | α-amidated residue |
|---|---|
| A alanine | b,o CRH; p Galanin; μ-Conotoxin |
| C cysteine | crustacean cardioactive peptide; conotoxins G1, M1, S1 |
| D aspartic | deltorphin |
| E glutamic | joining peptide |
| F phenylalanine | FMRF-NH$_2$; gastrin; cholecystokinin; CGRP; γ$_1$MSH |
| G glycine | oxytocin; vasopressin; GnRH; pancreastatin; leucokinin I, II; Manduca adipokinetic hormone; leucokinin I, II |
| H histidine | Apamin; scorpion toxin II |
| I isoleucine | h,r CRH; PHI; Manduca diuretic hormone; rat neuropeptide EI (melanin concentrating hormone) |
| K lysine | ELH; cecropin A; PACAP38[a], conotoxin GIA |
| L leucine | b,h GHRH; b-amidorphin; mastoparan; cecropin B; buccalin; myomodulin; PACAP27; proglucagon (111–123) |
| M methionine | Substance P; Substance K; PHM; gastrin releasing peptide; neurokinin A,B; neuromedin B, C |
| N asparagine | VIP (mammalian); neuromedin U; corazonin; mast cell degranulating peptide |
| P proline | calcitonin; TPH |
| Q glutamine | melittin; levitide |
| R arginine | preproglucagon (89–118) |
| S serine | frog granuliberin-R |
| T threonine | rat galanin; avian VIP; locust adipokinetic hormone |
| V valine | αMSH; r,p,h secretin; metorphamide/adrenorphin |
| W tryptophan | cockroach myoactive peptide, sea anemone peptide; crustacean erythrophore concentrating peptide |
| Y tyrosine | NPY; PYY; PP; ω-conotoxin; amylin |

[a]PACAP, pituitary adenylate cyclase activating peptide.

(See: "The Biosynthesis of Neuropeptides: Peptide α-amidation" Eipper, B. A., Stoffers, D. A. and Mains, R. E. (1992) Ann. Rev. Neurosci. 15, 57–85).

An example of a biologically active peptide which is of medical and commercial interest is calcitonin. This is a 32 amino active peptide which contains a single disulphide bridge and is amidated at the carboxy terminus. It is highly functionally conserved between species and the molecule obtained from salmon is in widespread use for human therapeutic applications. Medical conditions treated with salmon calcitonin include Paget's disease, hypercalcaemic shock and, more recently, osteoporosis.

One of the most important considerations in the practice of the invention is the choice of fusion partner with which to make the fusion protein. The fusion partner may be, and for preference usually will be, a natural protein, but it does not have to be. It is likely to be larger in size than a peptide sought to be produced by the invention. Proteins which themselves can be produced in high yields in milk, such as α$_1$-antitrypsin, are likely to be useful fusion partners in the invention. For preference, though, the fusion partner will additionally be a protein which is naturally produced in milk, as it is reasonable to assume that a protein which is normally secreted into milk, and which can be produced at high levels, will continue to be so secreted and produced after a peptide has been fused to its carboxy terminus. The optimal choice of fusion partner is preferably such that the carrier protein-peptide combination can be simply purified from milk, the two molecules can be cleaved by a specific process, and the peptide then purified away from the fusion partner.

A particularly preferred fusion partner for the production of peptides in milk is α-lactalbumin. This is a naturally occurring protein which is secreted into the milk of the majority of species measured to date, reflecting its important biological functions. In addition to providing a source of amino acids to the suckling young, α-lactalbumin regulates the volume of the milk produced. It does this by modifying the substrate specificity of the enzyme galactosyl transferase which is present in the golgi apparatus of protein-secreting cells. In the presence of α-lactalbumin, galactosyl transferase activity switches from using glucosamine, normally found on glycoproteins, as the acceptor for galactose, to free glucose. Therefore the level of lactose (galactose chemically linked to glucose) is elevated which increases the osmolarity of the milk and draws in water to provide the milk volume (see, for example, the review on α-lactalbumin by Brew, K. and Grobler, J. A. (1992) in "Advanced Dairy Chemistry—1" (Ed., Fox, P.), pp 191–229 Elsevier, London).

α-lactalbumin is a small molecule of approximately 14,000 Daltons mass containing about 120 amino acids depending on the species. Its suitability as a fusion partner, from a structural point of view, is seen by comparing rat α-lactalbumin with that from other species. Rat alone has a seventeen amino acid carboxy terminal extension but is identical to the other variants in its biological activity. Therefore it is reasonable to assume that the carboxy terminus of other α-lactalbumins can be extended without causing significant structural or functional disruption. A further desirable structural characteristic of α-lactalbumin is that is highly cross-linked by three or four disulphide bridges, depending on the species, and is therefore chemically robust.

For the reason given above, non-rat α-lactalbumins are preferred for use in the invention. The α-lactalbumin may be that from any mammal which produces lactose-rich milk. Such animals include humans, cattle, goats and sheep. The human protein is usually preferred since it is naturally expressed at higher concentrations, but when cleavage is to be achieved by cyanogen bromide (discussed below) sheep α-lactalbumin is preferred as it contains no internal methionine residues.

If non-rat α-lactalbumin is used, it may be appropriate to add to the C-terminus of the α-lactalbumin at least some of the amino acids that form the C-terminal extension to rat α-lactalbumin. As mentioned above, rat is the only species documented so far whose α-lactalbumin has a C-teminal extension, and it may be that the C-terminal extension is designed to fit at this place, to take a teleological view of evolution, and therefore to be especially appropriate. At least the first one, two three, four or even more of the amino acids of the rat C-terminal extension may be present. The first four amino acids are Gly-Ala-Pro-Ala (SEQ ID NO: 1).

This provision of the rat α-lactalbumin C-terminal extension represents a second aspect of the invention, according to which there is provided at least the first two, three or four of the amino acids of the extension may be present, in increasing order of preference. Further amino acids, particularly constituting a specifically cleavable sequence (or amino acid) and a peptide, as described above, may be present.

Even apart from the presence of any C-terminal extension, is as noted above, there may be some variation in the sequence of a fusion partner protein from a natural sequence. Although natural, wild-type sequences (and consensus sequences in the case of allelic variants) of α-lactalbumin or other fusion partners are usually preferred, some variation from the natural sequence may be accommodated or, in some cases at least, desired, provided that the properties of the fusion partner are not compromised to an unacceptable degree. Amino acid homology of at least 90 or 95% will usually be appropriate, and generally not more than one or two amino acid changes will be preferred.

As previously mentioned, expression levels of thirty grams per liter of ovine milk are well within the reach of existing transgenic animal technology. Such levels should also be achievable for α-lactalbumin, which is a non-toxic endogenous protein. Also there is no reason to believe that such a level should not be feasible in the milk of other species. The small size of α-lactalbumin means that the relative yield of peptide is high per gram of fusion protein. A thirty amino acid peptide, for instance, fused to α-lactalbumin, which is about 120 amino acids (depending on species and the size of the cleavable linker), would yield one-fifth of a gram of peptide per gram of fusion protein, which is six grams per liter in the above example. By extrapolation, a herd of about seventeen transgenic cows producing thirty grams per liter of fusion protein and 10,000 liters of milk per year would yield approximately a metric tonne of purified peptide per year.

α-Lactalbumin also has an unusual property which forms the basis of a highly specific purification step. Each molecule binds two calcium ions at specific sites, one at high affinity and one more loosely. The removal of the higher affinity calcium ion by the addition of a chelating agent exposes a hydrophobic patch on the surface of the molecule which is covered when calcium rebinds. This property can be exploited to purify α-lactalbumin from other proteins since α-lactalbumin alone can be specifically displaced from a hydrophobic environment by supplying calcium ions. The specific displacement may achieved by chromatography, in which case α-lactalbumin is eluted from a hydrophobic chromatography matrix by the addition of an appropriately low concentration of calcium to the elution buffer. Other ways of achieving the specific displacement of α-lactalbumin include phase partition techniques, although other procedures may be envisaged as well.

In practice, α-lactalbumin can be purified to a very high degree from a whey fraction of milk by a single step. This involves removing all of the free and bound calcium by the addition of a chelating agent, binding the α-lactalbumin to a chromatography matrix modified with phenyl groups or otherwise rendered hydrophobic, washing to remove non-specifically bound proteins and specifically eluting the α-lactalbumin by re-adding calcium to the medium ("Metal-Ion-Dependent Hydrophobic-Interaction Chromatography of α-Lactalbumins" Lindahl, L. and Vogel, H. J. (1984) *Analytical Biochemistry* 140, 394–402). This purification method yields α-lactalbumin from bovine milk which is greater than ninety-five percent pure as judged by coomassie staining of SDS polyacrylamide gels. In some, but not all, cases, the extension of the α-lactalbumin may interfere and result in an inability of the fusion protein to be purified in this way. In such cases, the fusion protein may be purified using standard techniques taking advantage of other properties of the novel molecule.

Once purified from milk, an α-lactalbumin-peptide fusion protein can be cleaved by any suitable means. Typically, cleavage will be achieved chemically or by means of an enzyme. An example of the former is treatment with cyanogen bromide which breaks peptide bonds at the carboxyl side of methionine residues. The advantage of this method is that the reaction uses inexpensive reagents, but an important restriction is that only a single methionine can be present in the fusion molecule. Many naturally occurring peptides and indeed α-lactalbumin from numerous species contain methionines which would also be cleaved and this method would therefore be unsuitable. However this can be circumvented by carefully choosing the species of origin for the proteins. Ovine α-lactalbumin, for example, does not contain methionine; and neither does salmon calcitonin. Therefore a fusion protein made from these two components, linked via a single methionine residue, would be a suitable candidate for cleavage by cyanogen bromide. In the exceptional case of salmon calcitonin, which has an amino-terminal cysteine residue, efficient cyanogen bromide cleavage requires the prior sulphonation of the adjacent thiol. This prevents an irreversible side-reaction, and the thiol can be regenerated after the cleavage reaction is completed ("Production of Recombinant Salmon Calcitonin by in vitro Amidation of an *Escherichia coli* Produced Precursor Peptide" Ray M. V. L. et al. (1993) *Bio/Technology* 11 64–70). A variety of other chemical cleavage reactions are also possible and any of these could be applied to appropriately designed fusion molecules ("Current Developments in Chemical Cleavage of Proteins—Minireview") Han, K. K., Richard, C. and Biserte, G. (1983) *Int. J. Biochem.* 15, 875–884).

The second preferred method of cleaving the fusion protein to release the free peptide is to design the fusion protein in such a way that the carboxy-terminus of the fusion partner is linked to the amino terminus of the peptide via a sequence of amino acids which include a specific recognition site for enzymic cleavage which does not occur elsewhere in the molecule. Examples of such sites are the sequences Ile-Glu-Gly-Arg (SEQ ID NO: 2) and Asp-Asp-Asp-Asp-Lys (SEQ ID NO: 3), which are recognised and cleaved by blood factor Xa and enterokinase respectively. This approach has the advantage that the cleavage enzyme can by chosen by reference to its recognition sequence: certain enzyme recognition sequences, such as those quoted above, only occur very rarely in natural molecules. Having said that, if at least part of the cleavage sequence occurs naturally at the appropriate ends of the peptide or the fusion partner, then that fact can be captitalised on in the practice of the invention and any synthetic portion of the linker may be reduced, or omitted, as appropriate.

Linker sequences may contain more than the absolute minimum sequence necessary to direct cleavage. For example, in the case of a linker sequence designed to be cleaved by enterokinase, the activation peptide of trypsinogen, which is cleaved specifically by enterokinase, may be present. The sequence is Phe-Pro-Thr-Asp-Asp-Asp-Asp-Lys (SEQ ID NO: 4). Any C-terminal extension to the fusion partner, such as the rat α-lactalbumin extension discussed above, may also be regarded as part of the linker.

After cleavage, the peptide can readily be separated from the fusion partner by any convenient method. In the case of α-lactalbumin, the efficient removal of the redundant fusion partner after cleavage from the peptide can, in many cases, simply use the technique of calcium-induced selective displacement from a hydrophobic environment (for example by chromatography) described above.

In the practice of the present invention, fusion proteins are produced in the milk of transgenic animals. The design and production of DNA sequences which encode protein-peptide fusion proteins is well known to those skilled in the art (Sambrook et al., "Molecular Cloning—A Laboratory Manual", Cold Spring Harbor Laboratory Press, (2nd Edition) 1989). The α-lactalbumin coding sequences can be obtained by screening libraries of genomic material or reverse-translated messenger RNA derived from the animal of choice (such as sheep). These sequences are then cloned into an appropriate plasmid vector and amplified in a suitable host organism, usually E. coli. The DNA sequence encoding the peptide of choice would then be constructed, for example, by polymerase chain reaction amplification of a mixture of overlapping annealed oligonucleotides. If the production of a carboxy-terminal amido peptide was the objective then a glycine codon would also be introduced at the 3'-end of the sequence coding for the peptide. This material would then be joined to the 3'-end of the DNA encoding the α-lactalbumin with the inclusion of a short sequence including an appropriate fusion protein cleavage site. This entire construct, after checking that the desired sequence has been constructed, would be cloned into a suitable vector carrying control sequences suitable for the generation of transgenic animals.

After amplification of the vector, the DNA construct would be excised with the appropriate 5' and 3' control sequences, purified away from the remains of the vector and used to produce transgenic animals. Conversely, with some vectors, such as yeast artificial chromosomes (YACs), it is not necessary to remove the assembled construct from the vector; in such cases the amplified vector may be used directly to make transgenic animals.

According to a third aspect of the present invention, there is provided an isolated or recombinant DNA molecule encoding a fusion protein, the DNA sequence comprising a coding sequence having a first segment encoding a peptide coupled to second segment encoding a fusion partner protein, and wherein DNA between the first and second segments encodes a cleavable linker sequence, the coding sequence being operatively linked to a control sequence which enables the coding sequence to be expressed in the milk of a transgenic non-human placental mammal.

A DNA sequence which is suitable for directing production to the milk of transgenic animals carries a 5'-promoter region derived from a naturally-derived milk protein and is consequently under the control of hormonal and tissue-specific factors. Such a promoter is therefore most active in lactating mammary tissue. This promoter sequence may be followed by a (usually shorter) DNA sequence directing the production of a protein leader sequence which would direct the secretion of the fusion protein across the mammary epithelium into the milk. At the other end of the fusion protein construct a suitable 3'-sequence, preferably also derived from a naturally secreted milk protein, may be added. The 3'-sequence performs various poorly defined functions, one of which is to improve the stability of transcribed RNA and thus increase levels of translated protein. An example of suitable control sequences for the production of proteins in the milk of transgenic animals are those from ovine β-lactoglobulin; see, for example, WO-A-8800239 and WO-A-9005188, which describe these control sequences in particular, and more generally address the production of transgenic animals secreting proteins of interest in their milk.

According to a fourth aspect of the present invention, there is provided a transgenic non-human placental mammal, whose genome incorporates a transgene construct comprising a coding sequence having a first segment encoding a peptide coupled to second segment encoding a fusion partner protein, and wherein DNA between the first and second segments encodes a cleavable linker sequence, the coding sequence being operatively linked to a control sequence which enables the coding sequence to be expressed in the milk of the mammal.

The production of transgenic animals can now be performed using a variety of methods. The most common of these is pronuclear injection where the DNA, having first been purified away from vector sequences, is directly microinjected into the male pronucleus. This can be done with either genomic sequences or using cDNA constructs co-injected with a genomic sequence for an endogenous milk protein ("Rescuing Transgene Expression by Co-integration" Clark, A. J. et al. (1992) Bio/Technology 10 1450–1454; and WO-A-9211358). Examples of other methods include cytoplasmic injection into ova, transformation of totipotent stem cells or carriage of foreign DNA sequences by sperm ("Status of Research with Transgenic Animals" Pursel, V. G. and Rexroad, Jr. C. E. (1993) J. Anim. Sci. 71(Suppl. 3) 10–19). A wide variety of animals are suitable for transgenic expression in milk including cows, sheep, goats, rabbits and pigs. Essentially, any species which is domesticated and produces sufficient quantities of harvestable milk would be preferable for the production of fusion proteins such as α-lactalbumin-peptide fusion proteins.

According to a fifth aspect of the invention, there is provided an isolated or recombinant DNA molecule encoding a protein in accordance with the second aspect.

Preferred features of each aspect of the invention are as for each other aspect, mutatis mutandis.

The invention will now be illustrated by the following examples.

EXAMPLES

Example 1

The preferred embodiment of this invention is a fusion protein made from ovine α-lactalbumin joined via a single methionine residue at its carboxy terminus to salmon calcitonin which in turn would carry an extra glycine at the carboxy terminus to act as a substrate for the α-amidating enzyme. This fusion protein would then be purified from the milk of transgenic animals by phenyl hydrophobic interaction chromatography before being cleaved by treatment with acidic cyanogen bromide.

The DNA sequence encoding this construct would carry the 5'-β-lactoglobulin promoter region, the entire ovine α-lactalbumin coding sequence with all of the individual introns and exons and carrying an appropriate restriction site near the 3'-end for linking on the peptide construct. The DNA sequence coding for the peptide would start with the same linking restriction site and some joining nucleotides running into the linking methionine codon, a sequence coding for salmon calcitonin, without introns, a 3'-glycine codon, and the β-lactoglobulin 3-region.

Example 2

A fusion protein has the same fusion partners as that of Example 1 but uses an enterokinase cleavage site. This requires the fusion protein to carry the amino acid sequence Asp-Asp-Asp-Asp-Lys (SEQ ID NO: 3) between the carboxy terminus of the α-lactalbumin and the calcitonin. This would have to be produced by making appropriate changes in the DNA coding region. In this instance α-lactalbumin from any species would be suitable and calcitonin sequences which contain methionine, such as the human one, could also be used.

Example 3

The procedure of Example 2 is followed, except that the peptide is salmon calcitonin and the fusion partner is human α-lactalbumin. The linker sequence is Gly-Ala-Pro-Ala-Phe-Pro-Thr-Asp-Asp-Asp-Asp-Lys (SEQ ID NO: 5), for cleavage with enterokinase.

Example 4

A fusion protein can be prepared as described in Example 1 and purified from the milk of transgenic animals as follows.

A whey fraction of milk, generated for example by the addition of solid ammonium sulphate to 20% (by weight) followed by centrifugation at 10,000 g for 15 minutes, is treated to remove free calcium, by the addition of a sufficient EDTA to chelate all of the available calcium (35 mM in cows' milk), and subjected to a separation technique based on differential hydrophobic interaction, for instance, chromatography on a matrix derivatised with a phenyl group. An example of a suitable matrix is phenyl SEPHAROSE™ (Pharmacia). After washing in 50 mM Tris/Cl pH 7.4 containing 1 mM EDTA, the fusion protein is specifically eluted by changing the EDTA in the buffer for 1 mM calcium chloride.

Example 5

A purified fusion protein can be prepared as in Example 1 and purified as in Example 4 and then specifically cleaved with cyanogen bromide using the following conditions.

The protein is extensively dialysed against water to remove all buffer salts and then lyophilised. It is then redissolved in formic acid (70% by volume), and solid cyanogen bromide is added to the resulting solution to provide a suitable concentration (generally 1 to 10% by weight, preferably about 2%). The solution is then incubated for twenty-four hours at room temperature. The reagents are then removed by repeating the lyophilisation stage and the cleavage products redissolved in the EDTA containing buffer as described in Example 4. At this stage the purification step described in Example 4 is repeated to remove the liberated α-lactalbumin, which is retained by the phenyl column, from the peptide, which flows straight through. The peptide is now completely free of α-lactalbumin and uncleaved fusion protein and in a suitable buffer for further purification by reversed-phase chromatography or another appropriate clean-up step.

Example 6

A fusion protein may be prepared as described in Example 1 but under the control of the human or bovine 5'- and 3'-control sequences either from β-lactoglobulin or from any other suitable promoter involved in controlling the expression of milk proteins.

What is claimed is:

1. An isolated DNA molecule encoding a fusion protein, comprising a coding sequence having a first segment encoding a peptide operatively linked to a second segment encoding a fusion partner protein, the first and second segments being separated by DNA which encodes a cleavable linker sequence, the coding sequence being operatively linked to a mammary tissue-specific promoter which enables the fusion protein to be expressed in the milk of a transgenic non-human placental mammal, wherein the peptide encoded by said first segment of said coding sequence is 3–100 amino acids in length.

2. The isolated DNA molecule of claim 1, wherein said control sequence comprises a β-lactoglobulin promoter.

3. The isolated DNA molecule of claim 1, further comprising a β-lactoglobulin 3' untranslated sequence located at the 3' end of said coding sequence.

4. The isolated DNA molecule of claim 1, wherein the peptide encoded by said first segment of said coding sequence is post-translationally modified.

5. The isolated DNA molecule of claim 1, wherein the peptide encoded by said first segment of said coding sequence is α-amidated.

6. The isolated DNA molecule of claim 1, wherein the peptide encoded by said first segment of said coding sequence is calcitonin.

7. The isolated DNA molecule of claim 1, wherein the fusion partner protein encoded by said second segment of said coding sequence is $\alpha_1$-antitrypsin.

8. The isolated DNA molecule of claim 1, wherein the fusion partner protein is a protein which is naturally produced in milk.

9. The isolated DNA molecule of claim 8, wherein said fusion partner protein is α-lactalbumin.

10. The isolated DNA molecule of claim 1, wherein said cleavable linker sequence is Ile-Glu-Gly-Arg (SEQ ID NO:2).

11. The isolated DNA molecule of claim 1, wherein said cleavable linker sequence is Asp-Asp-Asp-Asp-Lys (SEQ ID NO:3).

12. An isolated DNA molecule encoding a non-rat α-lactalbumin, wherein said non-rat α-lactalbumin contains an extension at its C-terminus, said extension comprising at least the first four N-terminal amino acids that naturally occur in the C terminal extension of rat α-lactalbumin.

* * * * *